United States Patent
Radl et al.

(10) Patent No.: US 7,208,608 B2
(45) Date of Patent: Apr. 24, 2007

(54) METHOD OF MANUFACTURING AN AMORPHOUS FORM OF THE HEMI-CALCIUM SALT OF (3R,5R) 7-3-PHENYL-4-PHENYLCARBAMOYL-2-(4-FLUOROPHENYL)-5-ISOPROPYL-PYRROL-1-YLL-3, 5-DIHYDROXYHEPTANOIC ACID (ACTORVASTATIN)

(75) Inventors: Stanislav Radl, Prague (CZ); Jan Stach, Prague (CZ)

(73) Assignee: Zentiva A. S., Praha (CZ)

( * ) Notice: Subject to any disclaimer, the term of this patent is extended or adjusted under 35 U.S.C. 154(b) by 0 days.

(21) Appl. No.: 10/502,632

(22) PCT Filed: Jan. 30, 2003

(86) PCT No.: PCT/CZ03/00007

§ 371 (c)(1),
(2), (4) Date: Jul. 26, 2004

(87) PCT Pub. No.: WO03/068739

PCT Pub. Date: Aug. 21, 2003

(65) Prior Publication Data

US 2005/0131055 A1 Jun. 16, 2005

(30) Foreign Application Priority Data

Feb. 1, 2002 (CZ) ............... PV 2002-413

(51) Int. Cl.
C07D 207/337 (2006.01)
C07D 207/335 (2006.01)

(52) U.S. Cl. .................................... 548/537

(58) Field of Classification Search ............... 548/537
See application file for complete search history.

(56) References Cited

U.S. PATENT DOCUMENTS

| 4,681,893 A | 7/1987 | Roth |
|---|---|---|
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,298,627 A | 3/1994 | Butler et al. |
| 5,342,952 A | 8/1994 | Butler et al. |
| 5,397,792 A | 3/1995 | Butler et al. |
| 5,969,156 A | 10/1999 | Briggs et al. |
| 6,121,461 A | 9/2000 | McKenzie |
| 2002/0183378 A1* | 12/2002 | Aronhime et al. ......... 514/423 |
| 2003/0212279 A1* | 11/2003 | Tessler et al. ............. 548/537 |
| 2005/0119493 A1* | 6/2005 | Suri et al. ................. 548/537 |

FOREIGN PATENT DOCUMENTS

| EP | 0 839 132 B1 | 5/1998 |
|---|---|---|
| WO | 92 06968 | 4/1992 |
| WO | WO 00/71116 | 11/2000 |
| WO | 01 42209 | 6/2001 |
| WO | WO 200257228 A1 * | 7/2002 |
| WO | 02 083638 | 10/2002 |
| WO | WO 200283637 A1 * | 10/2002 |
| WO | WO 200283638 A1 * | 10/2002 |

OTHER PUBLICATIONS

Brower, Philip L. et al.: "The synthesis of (4R-cis)-1,1-dimethylethyl 6-cyanomethyl-2,2-dimethyl-1,3-dioxane-4-acetate, a key intermediate for the prepartaion of Cl-981, a high potent, tissue selective inhibitor of HMG-CoA reductase" Tetrahedron Letters (1992), 33(17), 2279-82, XP000608147, p. 2284, line 3—line 15; figure 1.

Kelvin L. Baumann et al, "The Convergent Synthesis of Cl-981, an Optically Active, Highly Potent, Tissue Selective inhibitor of HMG-CoA Reductase", Tetrahedron Letters, 1992, Vol. 33, No. 17, pp. 2283-2284.

\* cited by examiner

Primary Examiner—Kamal A. Saeed
Assistant Examiner—Nyeemah Grazier
(74) Attorney, Agent, or Firm—Oblon, Spivak, McClelland, Maier & Neustadt, P.C.

(57) ABSTRACT

A method of manufacturing an amorphous form of the hemi-calcium salt of (3R, 5R) 7-[3-phenyl-4-phenylcarbamoyl-2-(4-fluorophenyl)-5-isopropyl-pyrrol-1-yl]-3,5-dihydroxyheptanoic acid of formula (I), in which (3R, 5R) 7-[3-phenyl-4-phenylcarbamoyl-2-(4-fluorophenyl)-5-isopropyl-pyrrol-1-yl]-3,5-dihydroxyheptanoic acid or its salt with a cation $M^+$ wherein $M^{30}$ is either a cation of an alkali metal or an ammonium cation of formula $R_nN^{(+)}H_{(4-n)}$ wherein R is lower $C_1$–$C_5$ alkyl, n may reach values ranging between 0 and 3, is, without isolating the intermediate in the form of the hemi-calcium salt or of another salt, acid or lactone, converted, in a solution, by the treatment with the calcium salt or calcium hydroxide, or a calcium $C_1$–$C_5$ alcoholate, to the hemi-calcium salt, and the latter is precipitated with a $C_1$–$C_5$ hydrocarbon or dialkylether of formula $R_1OR_2$, wherein each of $R_1$ and $R_2$ is a $C_1$–$C_5$ alkyl group. The starting acid or its salt is prepared starting from (3R, 5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl) acetate of formula II.

4 Claims, 2 Drawing Sheets

METHOD OF MANUFACTURING AN AMORPHOUS FORM OF THE HEMI-CALCIUM SALT OF (3R,5R) 7-3-PHENYL-4-PHENYLCARBAMOYL-2-(4-FLUOROPHENYL)-5-ISOPROPYL-PYRROL-1-YLL-3, 5-DIHYDROXYHEPTANOIC ACID (ACTORVASTATIN)

This application is a 371 of PCT/CZ03/00007, filed on Jan. 30, 2003, which claims priority to foreign application CZECH REPUBLIC PV 2002-413, filed on Feb. 1, 2002.

TECHNICAL FIELD

The invention relates to a new method of manufacturing an amorphous form of the hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid, known under the non-proprietary name atorvastatin. The said drug is an important representative of hypolipidemic and hypocholesteric medicaments.

BACKGROUND ART

Atorvastatin (formula I) is manufactured according to published patents (U.S. Pat. Nos. 4,681,893; 5,003,080; 5,097,045; 5,103,024; 5,124,482; 5,149,837; 5,155,251; 5,216,174; 5,245,047; 5,248,793; 5,273,995; 5,397,792; 5,342,952) usually from the sodium salt of (3R,5R) 7-[3-phenyl-4-phenylcarbamoyl-2-(4-fluorophenyl)-5-isopropyl-pyrrol-1-yl]-3,5-dihydroxyheptanoic acid and a suitable, water soluble calcium salt, preferably from calcium acetate or chloride.

The starting sodium salt of (3R,5R) 7-[3-phenyl-4-phenylcarbamoyl-2-(4-fluorophenyl)-5-isopropyl-pyrrol-1-yl]-3,5-dihydroxyheptanoic acid may be obtained from the said acid, which is normally obtained from (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)-acetate (formula II).

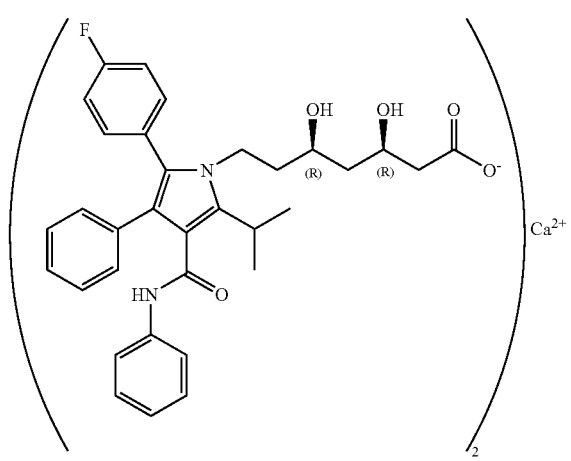

I

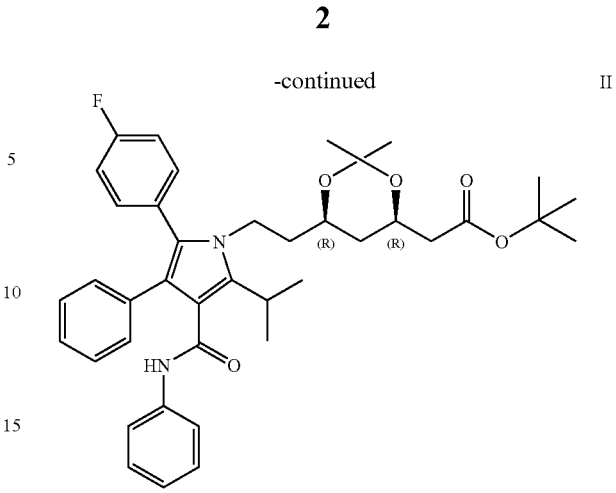

II

This key intermediate is converted to the sodium salt of the respective acid first by mixing with hydrochloric acid and, later on, with a large excess of sodium hydroxide, which is, however, accompanied with a large amount of excess hydroxide and also of sodium chloride. Acidification followed by extraction then affords a solution of the respective acid (formula III) without any inorganic impurities. Thus obtained acid is then converted to the respective lactone (formula IV), which can be purified by crystallization, and the purified lactone is then converted to the sodium salt by mixing with an equivalent of sodium hydroxide; an excess cannot be used as it would form, with the calcium salt, calcium hydroxide in the next step that could not be fully removed from the product in the follow up process steps according to the above patents. However, when an equivalent of the hydroxide is used the reaction is time consuming and it has to be monitored by HPLC. Another disadvantage of this process is loss of approximately 20% of the yield.

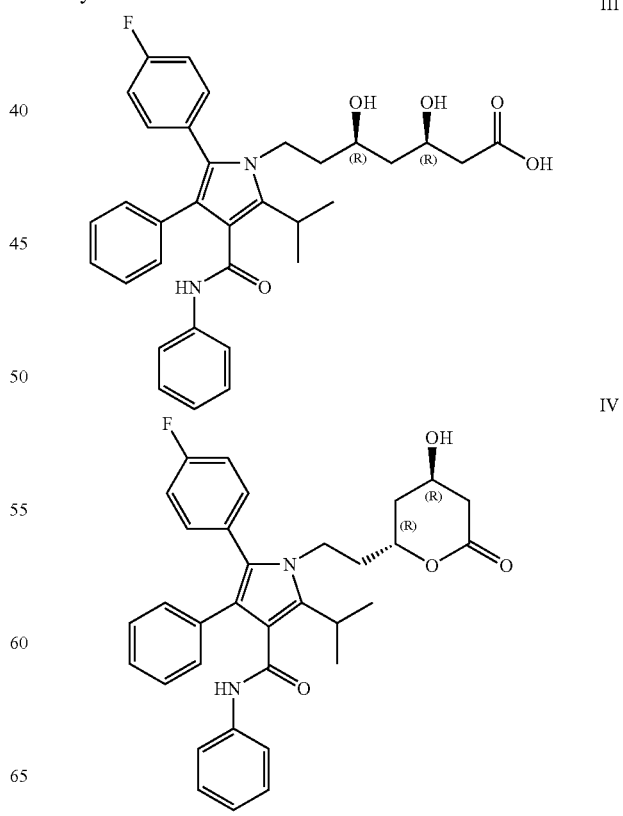

III

IV

Depending on the mode of carrying out, atorvastatin is obtained in some of its crystalline forms or as amorphous atorvastatin. In the original patents (for instance U.S. Pat. Nos. 4,681,893 and 5,273,995) there is no mention on the form of the substance obtained under these patents. Later patents (U.S. Pat. Nos. 5,969,156 and 6,121,461), disclosing crystalline forms of atorvastatin, suggest that the substance obtained according to the original patents was amorphous. Patent EP 839,132, disclosing a new method of obtaining the amorphous form of atorvastatin by dissolving crystalline atorvastatin of form I in a non-hydroxylated solvent (the patent mentions tetrahydrofuran and a mixture of tetrahydrofuran and toluene as examples of such solvents) followed by drying, repeats again that the original patents result in amorphous atorvastatin, but that such method is difficult to reproduce. According to our experience, atorvastatin obtained according to previous patents (U.S. Pat. Nos. 4,681,893, 5,298,627 and 5,273,995) is not perfectly amorphous and according to an X-ray analysis it shows the presence of crystalline components (see FIG. 1). The original patent U.S. Pat. No. 4,681,893 also describes a possibility of the purification of the unsuitable substance by dissolving in ethyl acetate, filtration through supercel and precipitation of the solution with hexane at 50° C. A patent to Ranbaxy Laboratories (WO 00/71116 A1) discloses conversion of the crystalline form of atorvastatin in a non-hydroxylated solvent and precipitation of the resulting solution with a non-polar hydrocarbon solvent. A similar approach is described in a patent to Lek (WO 01/42209 A1), which describes conversion of the crystalline form of atorvastatin to the amorphous form by dissolving in a variety of solvents including both non-hydroxylated solvents and lower alcohols, followed by precipitation of these solutions with solvents in which atorvastatin is insoluble. Again, such solvents are broadly defined and, in addition to non-polar hydrocarbon solvents, they include aliphatic ethers.

The objective of this invention is to describe a new improved method of manufacturing an amorphous form of the hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid that would not show the disadvantages of the above mentioned processes.

DISCLOSURE OF THE INVENTION

The benefits of the amorphous atorvastatin for some applications were stressed in the above-mentioned patent EP 839,132. The subject-matter of the present invention is a new method of manufacturing an amorphous form of the hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid, consisting in conversion of (3R,5R) 7-[3-phenyl-4-phenylcarbamoyl-2-(4-fluorophenyl)-5-isopropyl-pyrrol-1-yl]-3,5-dihydroxyheptanoic acid or its salt containing cation $M^+$ wherein $M^+$ is either an alkali metal cation or an ammonium cation of formula $R_nN^{(+)}H_{(4-n)}$ wherein R is a lower alkyl $C_1$–$C_5$, n may reach values ranging between 0 and 3, without isolating the intermediate in the form of the hemi-calcium salt or of another salt, acid or lactone, in a solution by the treatment of a calcium salt or of calcium hydroxide, or of a calcium $C_1$–$C_5$ alcoholate, to the hemi-calcium salt, followed by the precipitation thereof with a $C_5$–$C_{12}$ hydrocarbon or a dialkylether of formula $R_1OR_2$, wherein each of $R_1$ and $R_2$ is a $C_1$–$C_5$ alkyl group, thus forming a solid amorphous phase.

The whole process as above is based on a surprising finding that in ethyl acetate and in some related solvents not only the free acid corresponding to atorvastatin, but also a number of its salts, for instance the sodium salt, the potassium salt, ammonium salts derived from ammonia, primary, secondary and tertiary amines, and also the hemi-calcium salt itself are easily soluble.

A more detailed description of the invention follows.

The amorphous form of atorvastatin is preferably obtained directly by precipitation of a solution of the hemi-calcium salt of atorvastatin in a suitable solvent, preferably in an ester of a $C_1$–$C_5$ acid and a $C_1$–$C_5$ alcohol, using ethyl acetate being particularly advantageous, with a non-polar solvent, preferably with pentane, hexane, heptane or cyclohexane, optionally with a dialkylether $R_1OR_2$ wherein each of $R_1$ and $R_2$ is a $C_1$–$C_5$ alkyl group, preferably with diethylether, diisopropylether or t-butyl-methylether. In order to increase purity of the product it has been proven as useful to dilute the atorvastatin solution in ethyl acetate, prior to precipitation, with an additional co-solvent, for instance toluene, tert-butylmethylether or tetrahydrofuran, in an amount of from 5 to 95%, preferably from 30 to 70%. The amorphous form can also be obtained using a reversed process, wherein a solution of the hemi-calcium salt in a suitable solvent is added to one of the above-mentioned non-polar solvents. In none of the previous stages of this process, the hemi-calcium salt is not isolated in the solid state and, therefore, none of the patents protecting individual crystalline forms of this substance or processes of conversion of crystalline atorvastatin to amorphous atorvastatin can be infringed.

The solution of the hemi-calcium salt of atorvastatin in a suitable solvent, preferably in an ester of a $C_1$–$C_5$ acid and a $C_1$–$C_5$ alcohol, more preferably in ethyl acetate, can be obtained from a solution of the corresponding free acid, obtained using the previously described method from intermediate II. This solution is converted to the solution of the hemi-calcium salt by shaking with an aqueous solution of calcium hydroxide, with a suspension of calcium hydroxide in a smaller amount of water or, optionally, with a solution of a calcium $C_1$–$C_5$ alcoholate in a suitable solvent, preferably in the respective alcohol. Another possibility is to use a solution of any of the above salts of atorvastatin in a suitable solvent, preferably in ethyl acetate, and to convert it to a solution of the hemi-calcium salt of atorvastatin by shaking with a suitable water soluble calcium salt, preferably with calcium acetate. The excess of the used salts can then be simply removed by washing of the organic solution of the hemi-calcium salt of atorvastatin with water or with some aqueous solutions, for instance brine, and subsequently with water. Depending on the used precipitation system and the precipitation method, the solution of the hemi-calcium salt of atorvastatin will be then used in the next step without drying or it may be pre-dried with a suitable desiccant, preferably with sodium, calcium or magnesium sulphates.

Suitable water-soluble salts of atorvastatin can be advantageously obtained from a solution of the corresponding free acid obtained using the previously described method from the intermediate of formula II. This solution is then converted to the respective salt by adding a solution of an alkali hydroxide in water, by adding a solution of ammonia in water or a solution of the respective amine in water, followed by shaking. Preferably, amines such as triethylamine that are liquid at the normal temperature are used, which can be added to the solution of the respective free acid without using a solvent. The solutions of the above salts obtained in this way can be used directly, without any purification, for conversion to the solution of the hemi-calcium salt of atorvastatin as described above. The solutions of some of the above salts of atorvastatin can also be evaporated in this stage and purified by crystallization in suitable solvents. A solution of the sodium or potassium salts of atorvastatin can be advantageously obtained also directly from the solution after processing of the reaction of conversion of the intermediate of formula II. In the final stage a solution containing the respective alkaline metal chloride, the sodium or potassium salt of atorvastatin and an excess of the used alkaline hydroxide is obtained. It was surprisingly found out that by repeated extraction of this solution with a suitable solvent, preferably an ester of a $C_1$–$C_5$ acid and a $C_1$–$C_5$ alcohol, more preferably ethyl acetate, the respective salt can almost quantitatively be transferred to the organic phase and the latter can be used for further processing as described above.

An X-ray difractogram of atorvastatin prepared by the procedure described in the present invention is indicative of entirely amorphous structure (see FIG. 2).

The invention is further illustrated in annexed drawings and in the following examples. The examples, which illustrate preferable alternatives of the manufacture of atorvastatin of this invention, are of an illustrative character only and do not restrict the scope of the invention in any respect.

EXAMPLES

Example 1

Figure 1:
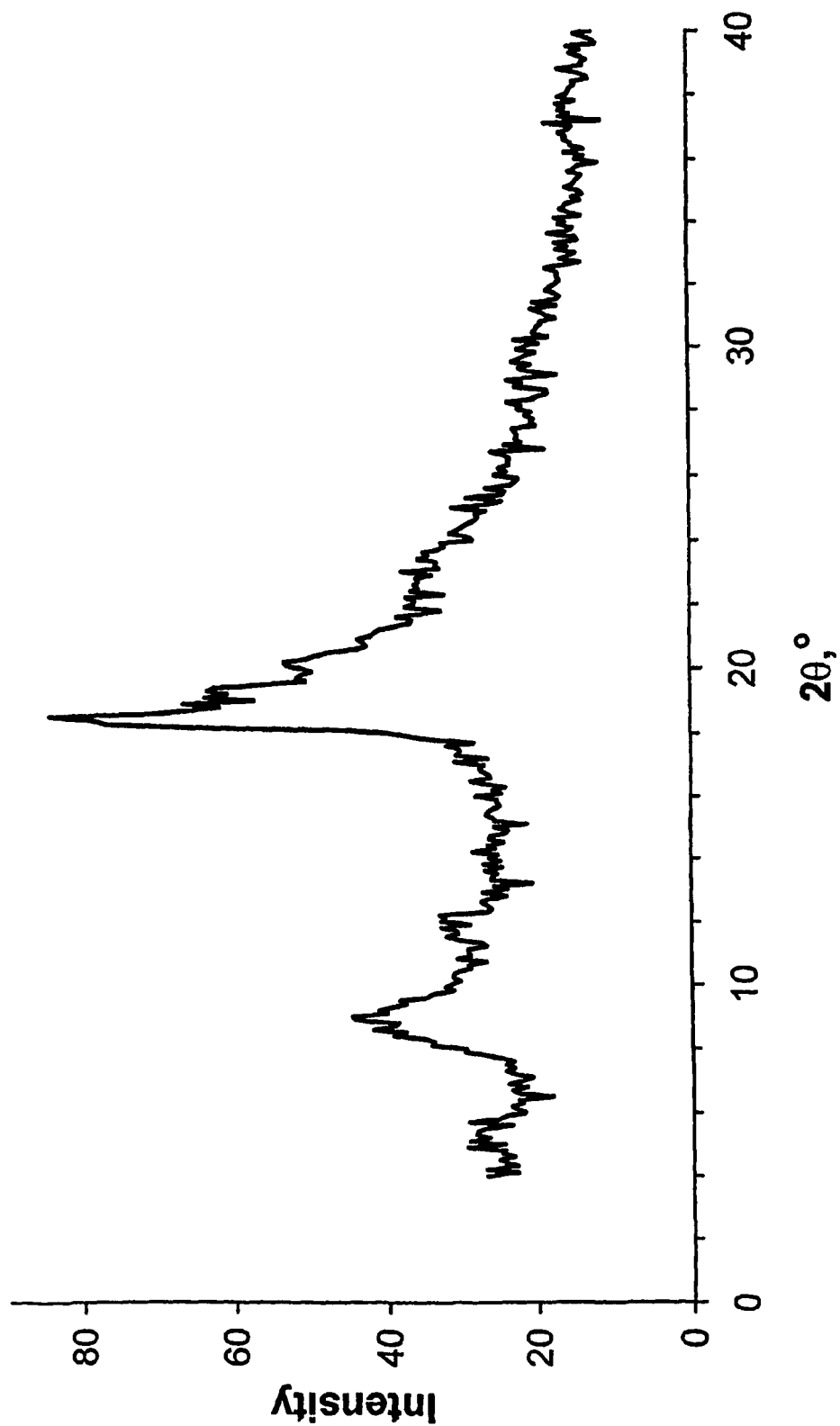
FIG. 1 depicts an X-ray difractogram of atorvastatin prepared by the procedure described in U.S. Pat. No. 5,298,627.
Figure 2:
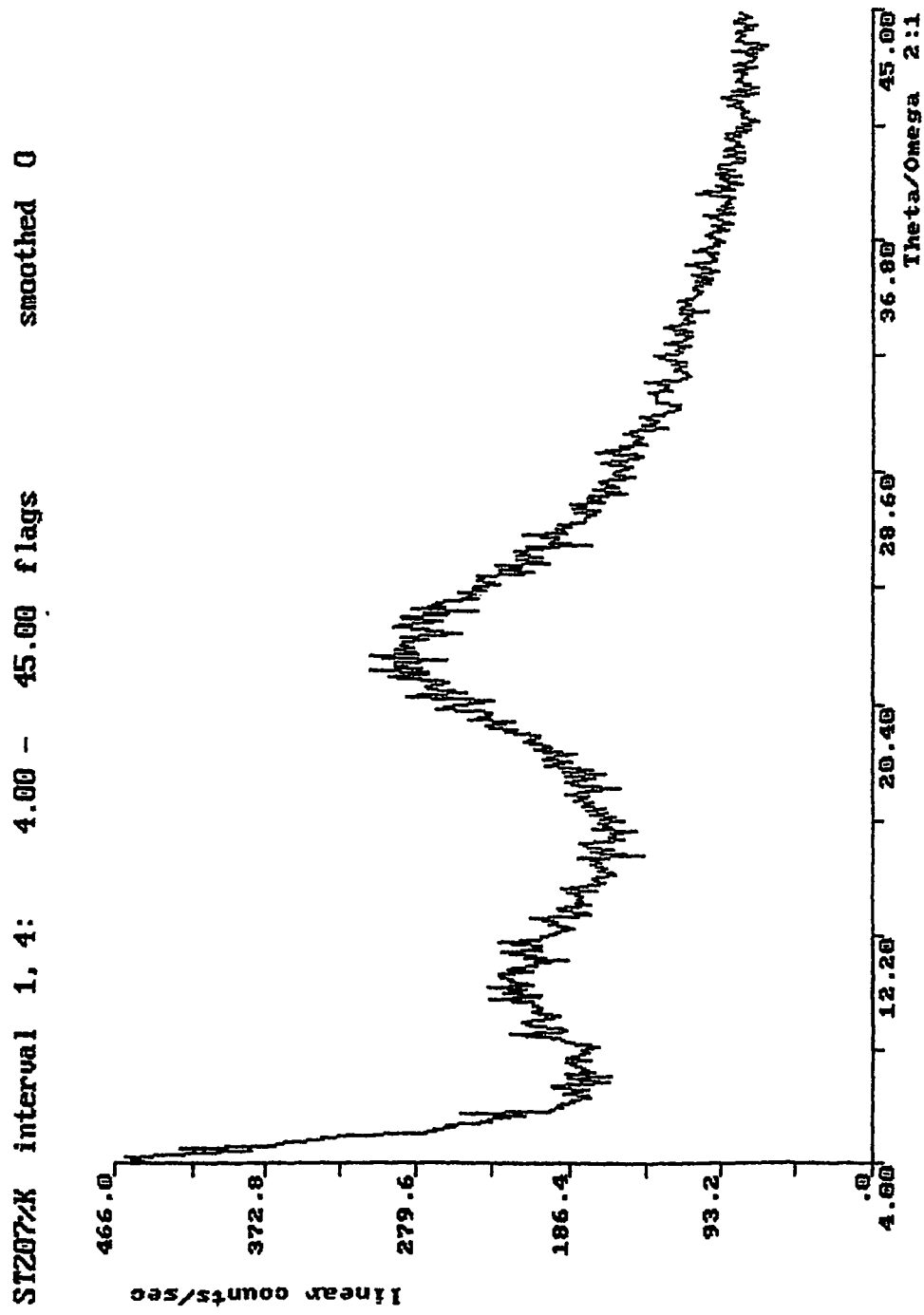
FIG. 2 depicts an X-ray difractogram of atorvastatin prepared by the procedure described in the present invention.

To the weighed ester of formula II (5 g, 7.6 mmol) tetrahydrofuran (75 ml) is added and, after all the substance has dissolved, 10% HCl (17 ml) is added. The mixture is stirred at the laboratory temperature for 6 hours. To the obtained solution a solution of 40% NaOH (10 ml) is added in the course of 5 minutes so that the temperature does not exceed 35° C. and the heterogeneous mixture is stirred intensively for 15 hours and, thereafter, poured into a separatory funnel containing demineralised water (150 ml) and hexane (50 ml). After shaking, the organic layer is removed and the aqueous layer is extracted with a mixture of hexane (40 ml) and tetrahydrofuran (10 ml). After the complete separation, the aqueous layer is extracted with ethyl acetate (1×40 ml, 4×20 ml). The ethyl acetate extract is then gradually shaken 3 times with demineralized water (5 ml), containing always 1 g of calcium acetate in 5 ml of water. The resulting ethyl acetate extract is washed with demineralized water (2×5 ml), concentrated in a vacuum evaporator to the volume of 20 ml. After filtration, the clear solution is added drop-wise to hexane (200 ml) under vigorous stirring over 5 minutes and then the mixture is stirred for another 20 minutes, the insoluble fraction is sucked away, washed with hexane (20 ml) and dried in vacuum at the laboratory temperature. 4.1 g of amorphous atorvastatin is obtained.

Example 2

Using the process described in Example 1, wherein potassium hydroxide instead of sodium hydroxide was used for the hydrolysis of the ester, thus obtaining the potassium salt of atorvastatin, which was further processed according to the procedure described in Example 1.

Example 3

To the weighed ester of formula II (5 g, 7.6 mmol) tetrahydrofuran (75 ml) is added and, after all the substance has dissolved, 10% HCl (17 ml) is added. The mixture is stirred at the laboratory temperature for 24 hours. To the solution a solution of 40% NaOH (10 ml) is then added in the course of 5 minutes and the heterogeneous mixture is stirred intensively for 17 hours and, thereafter, poured into a separatory funnel containing demineralised water (150 ml) and hexane (50 ml). After shaking, the organic layer is removed and the aqueous layer is extracted with a mixture of hexane (40 ml) and tetrahydrofuran (10 ml). After the complete separation, the aqueous layer is extracted with ethyl acetate (1×40 ml, 3×20 ml). After evaporating the extract 4 g of the sodium salt of atorvastatin are obtained. After re-crystallizing from ethanol, the salt is dissolved in ethyl acetate (100 ml) and the ethyl acetate solution is gradually shaken 3 times with demineralized water (5 ml), containing always 1 g of calcium acetate in 5 ml of water. The resulting ethyl acetate solution is washed with demineralized water (2×5 ml) and, after being dried with magnesium sulphate, it is concentrated in a vacuum evaporator to the volume of 30 ml. After filtration, the clear solution is added drop-wise to hexane (300 ml) under vigorous stirring over 5 minutes and then the mixture is stirred for another 20 minutes, the insoluble fraction is sucked away, washed with hexane (20 ml) and dried in vacuum at the laboratory temperature. 3.1 g of amorphous atorvastatin is obtained.

Example 4

To the weighed ester of formula II (5 g, 7.6 mmol) tetrahydrofuran (75 ml) is added and, after all the substance has dissolved, 10% HCl (17 ml) is added. The mixture is stirred at the laboratory temperature for 24 hours. To the solution a solution of 40% NaOH (10 ml) is then added in the course of 5 minutes and the heterogeneous mixture is stirred intensively for 17 hours and, thereafter, poured into a separatory funnel containing demineralised water (150 ml) and hexane (50 ml). The aqueous layer is acidified with 10% HCl to pH=3 and extracted with ethyl acetate (4×20 ml). The obtained extract is mixed with a mixture of calcium hydroxide (0.87 g) in demineralized water (15 ml) for 20 minutes. Then the aqueous layer is separated, the extract is washed with demineralized water (2×5 ml) and dried with magnesium sulphate (10 g) for 1 hour. To the dried extract hexane (160 Ml) is added under stirring and the resulting insoluble fraction is sucked away after 1 hour. After drying up, 3.3 g of amorphous atorvastatin is obtained.

Example 5

In the procedure described in Example 4, wherein a solution of calcium methanolate in methanol is used instead of calcium hydroxide for the conversion of the atorvastatin acid to its calcium salt, an analogous amount of amorphous atorvastatin is obtained after the processing described in Example 4.

Example 6

The weighed quantity of the ester of formula II (8.7 g, 13.3 mmol) is added to a round-shaped flask containing a mixture of tetrahydrofuran (100 ml) and 10% HCl (30 ml, 0.082 mol) under stirring and the resulting solution is stirred at the laboratory temperature for 24 hrs. Thereafter, in the course of 15 minutes, a 30% solution of NaOH (24 ml, 7.2 g, 0.18 mol) is added drop-wise to the solution; the reaction mixture will self-heat up and become cloudy. This mixture is stirred at the laboratory temperature for 15 hours and, thereafter, it is poured into a separatory funnel containing hexane (100 ml) and demineralized water (300 ml). After thorough shaking and separation of layers the bottom aqueous layer is shaken with additional hexane (2×50 ml). The washed aqueous layer is acidified with 10% HCl to pH=4 and extracted with dichloromethane (1×100 ml, 2×50 ml, 2×25 ml), the organic layer is washed with saturated brine (2×25 ml) and dried with $CaSO_4$ (25 g) overnight. Thereafter, the desiccant was filtered away, washed with dry dichloromethane (50 ml) and to the resulting solution a solution of triethylamine (3 ml, 21.5 mmol) in dry dichloromethane (20 ml) is added and the solution was evaporated to dryness in a rotary vacuum evaporator after stirring at the laboratory temperature for 0.5 hr. The resulting solid foam (ca 10 to 11 g) was mixed with dry dichloromethane (25 ml) and evaporated to dryness again (ca 9 g). This procedure was repeated once more to obtain 8.34 g of yellowish solid foam of the triethylammonium salt (12.6 mmol, 95%). The triethylammonium salt is dissolved in ethyl acetate (50 ml) and the solution is transferred to a separatory funnel. A solution of calcium acetate monohydrate (1.2 g, 6.8 mmol) in demineralized water (10 ml) is there added and the content of the separatory funnel is shaken. After the separation the aqueous layer is removed, the organic layer is shaken with water (2×10 ml) and dried with magnesium sulphate. After the separation, the organic layer is diluted with toluene (50 ml) and, under intensive stirring at the laboratory temperature, hexane (25 ml) is added drop-wise. Thereafter, the temperature of the mixture is increased to 50° C. and the mixture is stirred at this temperature until the primarily formed turbidity has been dissolved. Under intensive stirring, the temperature is let to drop spontaneously to 30° C. (some turbidity is formed again) and, at this temperature, hexane (100 ml) is added drop-wise without any further heating. Thereafter, the mixture is stirred at the laboratory temperature for another 10 minutes, the remaining quantity of hexane (100 ml) is added drop-wise and the mixture is stirred at the laboratory temperature for 1 hr. Atorvastatin, separated in this way, is sucked away, washed with hexane (25 ml), dried in vacuum up to constant weight and then triturated in an agate bowl. 5.6 g of amorphous atorvastatin is obtained.

Example 7

The weighed quantity of the ester of formula II (1 g) is added to a mixture of tetrahydrofuran (20 ml) and 10% HCl (3.5 ml) under stirring and the resulting solution is stirred at the laboratory temperature for 10 hrs. Thereafter, in the course of 15 minutes, a 40% solution of NaOH (2 ml) is added drop-wise to the solution and this mixture is stirred at the laboratory temperature for 15 hrs and, thereafter, it is poured into a separatory funnel containing hexane (10 ml) and demineralized water (30 ml). After thorough shaking and separation of layers the bottom aqueous layer is shaken with additional hexane (2×5 ml). The washed aqueous layer is acidified with 10% HCl to pH=4 and extracted with diethyl ether (2×10 ml, 2×5 ml), the organic layer is washed with saturated brine (2×5 ml) and dried with $Na_2SO_4$. Thereafter, the desiccant was filtered away, washed with dry diethyl ether and to the resulting solution triethylamine (0.3 ml) is added and the solution was evaporated to dryness in a rotary vacuum evaporator after stirring at the laboratory temperature for 0.5 hr. The resulting solid foam was mixed with dry diethyl ether (25 ml) and evaporated to dryness again (ca 0.9 g). The triethylammonium salt is dissolved in ethyl acetate (10 ml) and the solution is transferred to a separatory funnel. A solution of calcium acetate monohydrate (0.13 g) in demineralized water (1 ml) is there added and the content of the separatory funnel is shaken. After the separation the aqueous layer is removed, the organic layer is shaken with water. After the separation, pentane is added drop-wise to the organic layer under intensive stirring at the laboratory temperature. After dropping of ca 3 ml of pentane the solution turns remarkably cloudy and the mixture is stirred at the laboratory temperature for 15 minutes. Thereafter, additional 7.5 ml of pentane are rapidly added drop-wise, the mixture is stirred at the laboratory temperature for 1 hr and then left to stay overnight. Atorvastatin, separated in this way, is sucked away, washed with pentane (2 ml), dried in the air until constant weight and then triturated in an agate bowl. 0.6 g of amorphous atorvastatin is obtained.

Example 8

Using the method described in Example 7, wherein ethyl acetate was used instead of diethyl ether for the extraction of the acid, an analogous amount of amorphous atorvastatin is obtained.

Example 9

Using the method described in Example 7, wherein hexane is used instead of pentane for the precipitation, an analogous amount of amorphous atorvastatin is obtained.

Example 10

Using the method described in Example 7, wherein heptane is used instead of pentane for the precipitation, an analogous amount of amorphous atorvastatin is obtained.

Example 11

Using the method described in Example 7, wherein cyclohexane is used instead of pentane for the precipitation, an analogous amount of amorphous atorvastatin is obtained.

Example 12

Using the method described in Example 7, wherein diethyl ether is used instead of pentane for the precipitation, an analogous amount of amorphous atorvastatin is obtained.

Example 13

Using the method described in Example 7, wherein diisopropyl ether is used instead of pentane for the precipitation, an analogous amount of amorphous atorvastatin is obtained.

Example 14

Using the method described in Example 7, wherein tert-butyl methyl ether is used instead of pentane for the precipitation, an analogous amount of amorphous atorvastatin is obtained.

Example 15

Using the method described in Example 7, wherein, prior to the precipitation with hexane, the ethyl acetate solution of atorvastatin is diluted with 5 ml of toluene.

Example 16

Using the method described in Example 7, wherein, prior to the precipitation with hexane, the ethyl acetate solution of atorvastatin is diluted with 3 ml of tert-butyl methyl ether.

Example 17

Using the method described in Example 7, wherein, prior to the precipitation with hexane, the ethyl acetate solution of atorvastatin is diluted with 10 ml of tetrahydrofuran.

Example 18

The weighed quantity of the ester of formula II (1 g) is added to a mixture of tetrahydrofuran (15 ml) and 10% HCl (3.5 ml) under stirring and the resulting solution is stirred at the laboratory temperature for 24 hrs. Thereafter, in the course of 15 minutes, a 40% solution of NaOH (2 ml) is added drop-wise to the solution and this mixture is stirred at the laboratory temperature for 17 hrs and, thereafter, it is poured into a separatory funnel containing hexane (10 ml) and demineralized water (30 ml). After thorough shaking and separation of layers the bottom aqueous layer is shaken with additional hexane (2×5 ml). The washed aqueous layer is acidified with 10% HCl to pH=4 and extracted with dichloromethane (1×10 ml, 2×5 ml), to the organic layer triethylamine (0.3 ml) is added and the layer is dried with MgSO$_4$. Thereafter, the desiccant was filtered away, washed with dry dichloromethane and the combined organic solutions were evaporated to dryness in a rotary vacuum evaporator until constant weight (ca 0.85 g). The triethylammonium salt is dissolved in ethyl acetate (10 ml) and the solution is transferred to a separatory funnel. A solution of calcium acetate monohydrate (0.13 g) in demineralized water (1 ml) is there added and the content of the separatory funnel is shaken. After the separation the aqueous layer is removed; the organic layer is shaken with water. After the separation, hexane is added drop-wise to the organic layer under intensive stirring at the laboratory temperature. Atorvastatin, separated in this way, is sucked away, washed with hexane (2 ml), dried in vacuum until constant weight and then triturated in an agate bowl. 0.6 g of amorphous atorvastatin is obtained.

Example 19

To the weighed ester II (5 g, 7.6 mmol) tetrahydrofuran (75 ml) is added and after all of the substance has dissolved, 10% HCl (17 ml) is added. The mixture is stirred at the laboratory temperature for 24 hrs. Thereafter, in the course of 5 minutes, a 40% solution of NaOH (10 ml) is added drop-wise to the solution and the heterogeneous mixture is stirred vigorosuly for 17 hrs and, thereafter, it is poured into a separatory funnel containing demineralized water (150 ml) and hexane (50 ml). After shaking and repeated extraction with hexane (50 ml) the aqueous layer is acidified with 5 ml of concentrated HCl and extracted with ethyl acetate (4×20 ml). After washing with brine (2×10 ml) triethylamine (1.5 ml) is added to the ethyl acetate extract is gradually shaken 3× with demineralised water (10 ml), containing always 1 g of calcium acetate in 10 ml of water. The resulting solution was washed with demineralised water (2×5 ml) and dried with magnesium sulphate (10 g) for 1 hour. Hexane (50 ml) is added to the dried extract under stirring and the resulting insoluble fraction is sucked away after stirring for 1 hour. Drying affords 3.35 g of amorphous atorvastatin.

Example 20

Using the method described in Example 19, wherein an equivalent amount of a 40% aqueous solution of methylamine is used instead of triethylamine.

Example 21

Using the method described in Example 19, wherein an equivalent amount of a 35% aqueous solution of ammonia is used instead of triethylamine.

The invention claimed is:

1. A method of manufacturing an amorphous form of the hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid of formula I

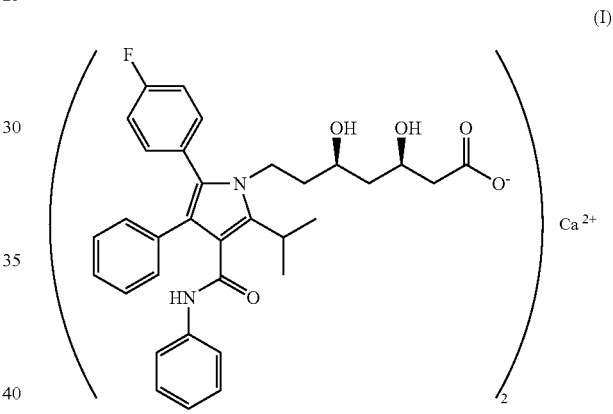

(I)

the method comprising,
extracting, with an ethylacetate, a water-containing solution of a sodium salt of (3R,5R) 7-[3-phenyl-4-phenylcarbamoyl-2-(4-fluorophenyl)-5-isopropyl-pyrrol-1-yl]-3,5-dihydroxyheptanoic acid, which is obtained by alkaline hydrolysis of a tert-butyl ester of formula II,

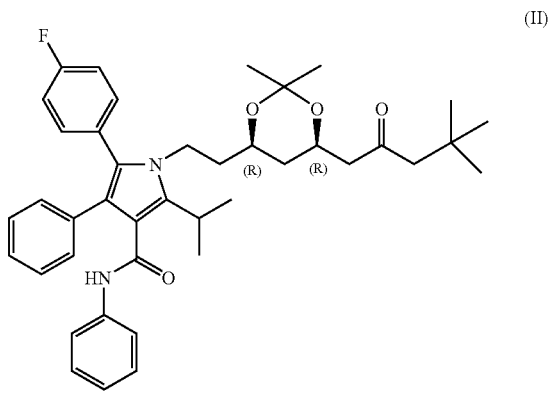

(II)

wherein the water-containing solution also contains reaction by-products;

reacting the resulting extract with an organic or inorganic calcium salt or hydroxide, optionally rinsing one or more times with water, and precipitating hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid of formula I with a C5–C12 hydrocarbon.

2. The method according to claim 1, wherein the C5–C12 hydrocarbon is pentane, hexane, heptane, cyclohexane, or their mixtures.

3. The method according to claim 1, wherein the resultant extract of hemi-calcium salt of (3R,5R) 7-[3-phenyl-4-phenylcarbamoyl-2-(4-fluorophenyl)-5-isopropyl-pyrrol-1-yl]-3,5-dihydroxyheptanoic acid of formula I and ethylacetate is diluted with 5 to 95% of one or more of tetrahydrofuran, tert-butyl methyl ether, and toluene.

4. The method according to claim 1, wherein the reaction by products are sodium hydroxide and sodium chloride.

* * * * *